United States Patent [19]
LaRoche Navarron

[11] 3,974,164
[45] Aug. 10, 1976

[54] RESERPIC ACID DERIVATIVES

[75] Inventor: Marguerite Séverine Lucie LaRoche Navarron, Levallois-Perret, France

[73] Assignee: Serdex-Societe d'Etudes, de Recherches, de Diffusion et d'Exploitation, Puteaux, France

[22] Filed: July 22, 1974

[21] Appl. No.: 490,509

[30] Foreign Application Priority Data
Aug. 2, 1973   United Kingdom............... 36820/73

[52] U.S. Cl......................... 260/287 A; 260/240 A; 260/240 G; 424/262
[51] Int. Cl.²..................................... C07D 401/04
[58] Field of Search......... 260/240 A, 240 G, 287 A

[56]         References Cited
         UNITED STATES PATENTS
2,990,407   6/1961   Velluz et al......................... 260/287

Primary Examiner—G. Thomas Todd
Attorney, Agent, or Firm—Young & Thompson

[57] ABSTRACT

The invention relates to compounds having the formula:

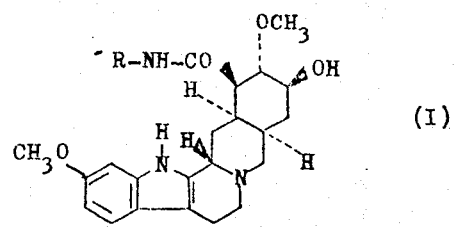

in which R is a group —$NHR_1$, —NH—$COOR_2$, —NH—CO—$R_3$, —NHCONH—Ar, —NH—CS—NH—Ar or —N=CH—Ar, $R_1$ being hydrogen, $R_2$ being lower alkyl or phenyl, $R_3$ being optionally substituted phenyl and Ar being optionally substituted phenyl, and their pharmaceutically acceptable acid addition salts.

Said compounds possess an anti-hypertensive activity.

4 Claims, No Drawings

RESERPIC ACID DERIVATIVES

This invention relates to reserpic acid derivatives and to a process for their preparation.

The compounds of this invention have the following general formula:

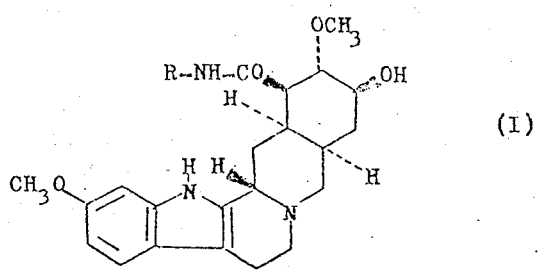

in which R is a group -NHR$_1$, —NH—COOR$_2$, —NH—CO—R$_3$, NH—CO—NH—Ar, —NH—CS—NH—Ar or —N=CH—AR in which:

R$_1$ is hydrogen,
R$_2$ is a lower alkyl or phenyl,
R$_3$ is phenyl optionally carrying one to three hydroxy or lower alkoxy (preferably methoxy),
Ar is phenyl optionally carrying one to three radicals selected independently from one another from nitro and lower alkoxy (preferably methoxy).

In the above definition, "lower alkyl or alkoxy" means radicals having 1–6 carbon atoms.

This invention includes also within its scope the pharmaceutically acceptable acid addition salts of the compounds of the formula (I) with inorganic or organic acids, particularly with hydrochloric acid.

The compound of the formula (I) in which R = —NH$_2$ may be prepared by reacting hydrazine of the formula NH$_2$—NH$_2$ with reserpine, to give reserpohydrazide. This reaction may be effected within a refluxing alcohol.

The other compounds are prepared from reserpohydrazide. Condensation of reserpohydrazide with an alkyl, aralkyl or aryl haloformate of the formula

X—COOR$_2$ (II)

gives compounds of the formula (I) in which R = —NH—COOR$_2$. This reaction may be effected within a refluxing alcohol.

Condensation of reserpohydrazide with a carboxylic acid chloride of the formula

R$_3$—COCl (III)

gives compounds of the formula (I) in which R = —NH—COR$_3$. This reaction may be effected within an anhydrous solvent at moderate temperature.

Condensation of reserpohydrazide with an aryl isocyanate or isothiocyanate

Ar—N=C—Y (IV)

in which Y = O or S, gives compounds of the formula (I) in which R = NH—CY—NH—Ar. This reaction may be effected within an alcoholic solvent, at moderate or boiling temperature.

Condensation of reserpohydrazide with an aldehyde of the formula

Ar—CHO (V)

gives compounds of the formula (I) in which R = —N=CH—Ar. This reaction may be effected within a refluxing alcoholic solvent.

Reserpine, which is the starting material, is a naturally occurring alkaloid which has been known for a long time and which may be extracted from plants such as *Rauwolfia serpentina* L. Benth. (cf. Dorfman et al., Helv. Chim. Acta, 1954, 37, 59; Schwyger, Mueller, U.S. Pat. 2,833,771 (1958)). Its synthesis was described by Woodward et al., (Tetrahedron, 1956, 78, 2023).

The following examples are given to illustrate the invention.

EXAMPLE 1

Reserpic acid hydrazide (R = —NH$_2$)

A mixture of reserpine (50 g) and 99% hydrazine hydrate (100 ml) in n-amyl alcohol (600 ml) is refluxed during 36 hours in the presence of a few drops of acetic acid. The reaction mixture is suction filtered hot, to separate the hydrazide from the 3,4,5-tri-methoxy-benzoic acid hydrazide which is formed simultaneously and which is soluble in the reaction medium. The reserpohydrazide recovered on the Buchner funnel is washed with boiling ethanol and is then recrystallized from pyridine. It is obtained as colorless bright prisms melting at 356°C.

| Analysis: C$_{22}$H$_{30}$O$_4$N$_4$ | C% | H% | N% |
|---|---|---|---|
| Calculated: | 63.7 | 7.3 | 13.5 |
| Found: | 63.8 | 7.3 | 13.4 |

Dihydrochloride

This hydrazide gives a colorless dihydrochloride melting at 271°C and highly water-soluble when heated during 10 minutes in a 96% ethanol solution saturated with gaseous hydrogen chloride.

| Analysis: C$_{22}$H$_{30}$O$_4$N$_4$ . 2 HCl | C% | H% | N% |
|---|---|---|---|
| Calculated: | 54.2 | 6.6 | 11.5 |
| Found: | 54.0 | 6.8 | 11.2 |

EXAMPLE 2

N'-(ethoxycarbonyl)reserpohydrazide (R = —NH—COOC$_2$H$_5$)

A suspension of 0.01 mole reserpohydrazide and 0.012 mole ethyl chloroformate in 50 ml absolute ethanol is stirred during one hour and is then refluxed during 10 minutes. After cooling, a stream of gaseous hydrogen chloride is bubbled through to saturation, the solvent is then removed in vacuo, the resulting residue is washed with boiling benzene and is then recrystallized from ethanol-benzene, to give the dihydrochloride, M.p. = 268°C.

EXAMPLE 3

N'-(butoxycarbonyl)reserpohydrazide (R = —NH—COOC₄H₉)

This compound is prepared as described in Example 2, from butyl chloroformate. It crystallizes as the dihydrochoride monohydrate. M.p. = 269°C.

EXAMPLE 4

N'-(isobutoxycarbonyl)reserpohydrazide (R = —NH—COOCH₂—CH—(CH₃)₂)

This compound is prepared as described in Example 2, from isobutyl chloroformate. It crystallizes as the monohydrochloride monohydrate. M.p. = 268°C.

EXAMPLE 5

N'-(isopropoxycarbonyl)reserpohydrazide (R = —NH—COOCH—(CH₃)₂)

This compound is prepared as described in Example 2, from isopropyl chloroformate. It crystallizes as the dihydrochloride. M.p. = 265°C.

EXAMPLE 6

N'-(phenoxycarbonyl)reserpohydrazide (R = —NH—COOC₆H₅)

This compound is prepared as described in Example 2, from phenyl chloroformate. It crystallizes as the monohydrochloride monohydrate. M.p. = 281°C.

EXAMPLE 7

N'-(3,4,5-trimethoxy-benzoyl)reserpohydrazide

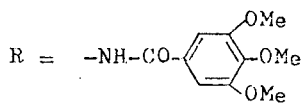

To a suspension of 0.02 mole reserpohydrazide in anhydrous methylene chloride maintained under magnetic stirring is added portion wise 3,4,5-trimethoxy-benzoic acid chloride (0.025 mole) dissolved in 50 ml of an anhydrous methylene chloride solution containing 20% anhydrous pyridine. The reaction mixture is then heated at about 35°–40°C during 5 minutes, part of the solvent is evaporated in vacuo, the resulting material is taken up into benzene, treated again in vacuo to remove the unreacted acid chloride and is then finally recrystallized from ethanol saturated with gaseous hydrogen chloride. Under such conditions, the dihydrochloride is obtained as cream-colored microcrystals melting at 246°C.

EXAMPLE 8

N'-(3,5-dimethoxy-1-hydroxy-benzoyl)reserpohydrazide

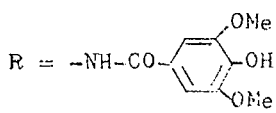

The dihydrochloride of this compound is obtained as described in Example 7, from syringic acid chloride. M.p. = 266°C.

EXAMPLE 9

N'-phenylcarbamoyl reserpohydrazide R = NH—CO—NH—C₆H₅

A suspension of reserpohydrazide (0.01 mole) and phenyl isocyanate (0.01 mole) in an azeotropic benzene-alcohol mixture (200 ml) is gently boiled during 2.5 hours, with magnetic stirring. After cooling, a stream of gaseous hydrogen chloride is bubbled through the reaction mixture to saturation, after which the solvent is evaporated in vacuo, to give the dihydrochloride which is recrystallized from benzene containing a few drops of ethanol as bright colorless prisms. M.p. = 242°C.

EXAMPLE 10

N'-phenylthiocarbamoyl reserpohydrazide R = NH—CS—NH—C₆H₅

A mixture of phenyl isothiocyanate (0.02 mole) and reserpohydrazide (0.02 mole) in absolute ethanol (100 ml) is stirred during 45 minutes, and it is then heated to about 50–60°C during 15 minutes. After cooling, a stream of gaseous hydrogen chloride is bubbled through the solution, after which the solvent is removed, the residue is washed with boiling benzene and is then recrystallized from ethanol-benzene, to give the dihydrochloride of the compound, as fine colorless needles. M.p. = 280°C, with decomposition.

EXAMPLE 11

N'-anisaldehyde reserpohydrazone

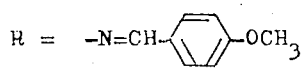

A mixture of anisaldehyde (0.02 mole) and reserpohydrazide (0.02 mole) is refluxed during 6–8 hours in absolute ethanol (100 ml). The solvent is then partly evaporated off: after cooling, the resulting precipitate is suction filtered and is then recrystallized from benzene containing a small amount of ethanol. The compound crystallizes with one molecule water. M.p. = 206°C; it loses its water at that temperature and resolidifies to melt again at 258°C.

EXAMPLE 12

N'-(3,4,5-trimethoxy-benzaldehyde)reserpohydrazone

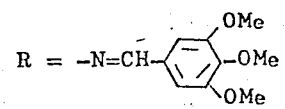

The compound is prepared as described in Example 11, from 3,4,5-trimethoxy-benzoic aldehyde. It crystallizes as the dihydrochloride from ethanol saturated with gaseous HCL. M.p. = 248°C.

EXAMPLE 13

N'(p-nitrobenzaldehyde)reserpohydrazone

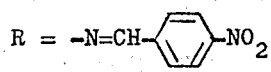

The compound is prepared as described in Example 11, from para-nitrobenzaldehyde. It crystallizes from ethanol as pale yellow micro-crystals. M.p. = 292°C, with decomposition from 260°C.

The invention provides also to a pharmaceutical composition having an anti-hypertensive activity, containing a therapeutically effective quantity of a compound of the formula (I) or a pharmaceutically acceptable salt thereof.

The results of pharmacological and toxicological tests demonstrating the anti-hypertensive activity and the low toxicity of the compounds of this invention, which are thus therapeutically valuable compounds, are reported below.

I — PHARMACOLOGICAL TESTS a. Tests in dogs

The tests were carried out in dogs of various races, of either sex, weighing from 10 to 25 kg. They were anesthetized with chloralose.

They were randomly distributed into two groups:

Group 1. Investigation of the action on the hemodynamics, respiration and systemic metabolism.

The animals were not submitted to assisted ventilation.

The femoral pressure was recorded at the right femoral artery with a STATHAM P 23 AA electromanometer. The ventilation rate was determined with a DRAGER recording volumeter. The gas breathed out was collected in a DOUGLAS tube.

The blood $pCO_2$, $pO_2$ and pH and also the $pO_2$ and $pCO_2$ of the gas breathed out were measured with a pH meter apparatus.

The cardiac rate of flow was determined according to FICK's method.

Group 2. Investigation of myocardial contractility

The animals were submitted to artificial respiration.

The contractility of the myocardium was recorded by means of a stress gauge attached to the wall of the right ventricle and the rate of increase of the isometric pressure of myocardium ($df/dt$) by differentiation of the force of contraction of the myocardium. The cardiac rhythm was recorded with an OFFNER BECKMAN cardiotachometer, the ECG with a Cardioline electrocardiograph.

The test materials were administered as aqueous solutions in isotonic sodium chloride solution.

The compounds of this invention, on intravenous administration at a single dosage of 5 or 10 mg/kg, produce no change in the ventilation rate. They stimulate oxygen consumption and, to a lesser extent, the production of $CO_2$. They decrease the respiratory quotient.

The compounds of this invention determine a depression of the systolic, diastolic, mean and differential blood pressures; this action is gradual and moderate, but of long duration: although moderate, the depression of the systolic, diastolic, mean and differential pressures is significant and stable 1–2 hours after administration of the test materials; it remains constant for a further very extended period of time. The test materials produce a substantial depression of the total peripheral strength and of the elastic strength of the arteries.

Before depressing same, the compounds of this invention stimulate the cardiac rate of flow, the systolic ejection rate, the cardiac and systolic indices, the work of the left ventricle and the systolic ejection work. They depress slightly the tension time index.

The increase of the force of contraction of the heart and of the rate of increase of the isometric pressure of the myocardium is moderate.

The compounds of this invention have no significant action on the cardiac rhythm.

b. Tests in rats

The experiments were carried out in white adult rats of WISTAR AH. strain weighing 200 g ± 10 g, normotensive or made hypertensive either with metacorticosteroids or according to the GROLLMAN method.

The blood pressure of the animals was determined by a non surgical method.

The compounds of this invention, suspended in gummy julep, were administered via the gastric route, either as single doses of 50 or 100 mg/kg p.o., or as repeated daily doses of 10 and 25 mg/kg p.o.

Under the experimental conditions selected, the compounds have no significant action on the blood pressures of normotensive rats. In contrast, they depress the blood pressures of hypertensive rats. This action is moderate but of long duration.

II — TOXICOLOGICAL TESTS

Immediate and delayed toxicity on administration of a single dose

The tests were carried out in adult white mice, of Swiss strain, weighing 20 ± 2 g.

The animals were kept fasting during 18 hours and were then distributed in homogeneous lots of 10 animals (5 male and 5 female) each.

a. Oral route

The test materials, suspended in gummy julep, were administered by stomach tube. The treated animals were kept under observation during 15 days.

Up to dosages of 3 g/kg, p.o., even of up to 5 g/kg, p.o., the compounds of this invention produced no fatal issue, either immediately or after 15 days of observation. The test animals exhibited no apparent change of behavior.

b. Intraperitoneal route

The test materials were used as aqueous solutions in sodium chloride isotonic solution. The test animals were kept under observation during 15 days.

Up to 1000 mg/kg i.p., the compounds of this invention produced no fatal issue and determined no apparent change in the behavior of the animals.

It is apparent from the data provided by the experiments conducted under the experimental conditions adopted, that the compounds of this invention prove to be long acting anti-hypertensive agents free from side-effects.

The compounds are advantageously administered orally. Any formulation suitable for this route of administration may be used.

Examples of pharmaceutical compositions are given below:

- Tablets with ordinary or enteral coating:

| | weak dose | strong dose |
|---|---|---|
| active ingredient | 25 mg | 50 mg |
| Excipients Talc | | |
| Magnesium stearate | | q.s. to make one tablet |
| Starch | | |
| PVP | | |
| Calcium sulfate | | |
| - Injectable ampullae | | |
| active ingredient (hydrochloride) | | 50 mg |
| physiological salt solution | | q.s. to make 1 ampulla. |

Having now described my invention what I claim as new and desire to secure by Letters Patent is:

1. A compound selected from the group consisting of the compounds having the formula:

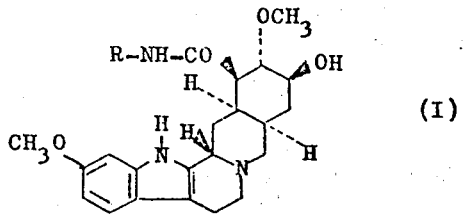

(I)

in which R is selected from the group consisting of the radicals of formula —$NHR_1$, —NH—$COOR_2$, —NH—CO—$R_3$, —NH—CO—NH—Ar, —NH—CS—NH—Ar and —N=CH—Ar in which:

$R_1$ is hydrogen, $R_2$ is selected from the group consisting of lower alkyl and phenyl, $R_3$ is selected from the group consisting of phenyl, phenyl mono-, di-, and tri-substituted by radicals selected from the group consisting of lower alkoxy and hydroxy, and Ar is selected from the group consisting of phenyl, phenyl mono-, di-, and tri-substituted by radicals selected from the group consisting of lower alkoxy and nitro, and their pharmaceutically acceptable addition salts with inorganic or organic acids.

2. Reserpohydrazide and an acid addition salt thereof with a pharmaceutically acceptable acid.

3. N'-(butoxycarbonyl)reserpohydrazide and an acid addition salt thereof with a pharmaceutically acceptable acid.

4. N'-isobutoxy carbonyl reserpohydrazide and an addition salt thereof with a pharmaceutically acceptable acid.

* * * * *